US007264773B2

(12) United States Patent
Adiga et al.

(10) Patent No.: US 7,264,773 B2
(45) Date of Patent: Sep. 4, 2007

(54) METHOD FOR BIOERADICATION USING FINE MIST OF BIOCIDE SOLUTIONS

(75) Inventors: Kayyani C. Adiga, Macon, GA (US); Rajani Adiga, Macon, GA (US)

(73) Assignee: Nanomist Systems, LLC, Warner Robins, GA (US)

( * ) Notice: Subject to any disclaimer, the term of this patent is extended or adjusted under 35 U.S.C. 154(b) by 661 days.

(21) Appl. No.: 10/428,345

(22) Filed: May 2, 2003

(65) Prior Publication Data

US 2004/0009094 A1 Jan. 15, 2004

Related U.S. Application Data

(60) Provisional application No. 60/377,156, filed on May 2, 2002.

(51) Int. Cl.
*A61L 2/22* (2006.01)
(52) U.S. Cl. .......................................... 422/28; 422/37
(58) Field of Classification Search ..................... None
See application file for complete search history.

(56) References Cited

U.S. PATENT DOCUMENTS

| 4,504,442 A | 3/1985 | Rosenblatt et al. |
| 4,681,739 A | 7/1987 | Rosenblatt et al. |
| 4,908,188 A | 3/1990 | Jefferis, III et al. |

(Continued)

FOREIGN PATENT DOCUMENTS

WO    WO99/66961 A1 * 12/1999

OTHER PUBLICATIONS

CDG Technology, Inc., Chlorine Dioxide for Gas Phase Decontamination, 2002, previously published at http://www.cdgtechnology.com/.

(Continued)

*Primary Examiner*—E. Leigh McKane
(74) *Attorney, Agent, or Firm*—Brian D. Bellamy (57) ABSTRACT

The invention provides a method for generating a homogeneous aqueous mist solution containing a solvent such as water and a biocide agent such as chlorine dioxide, which would otherwise be unstable. The unstable biocide agent or chlorine dioxide is quickly dissolved or mixed with a mist of solvent causing the biocide agent to co-exist or co-mist therewith. The mist microencapsulates the biocide gas so that it does not decompose in the fumigation volume or space. The resulting homogenous mist solution provides a mist for delivering the biocide agent in a chemically stable form.

Methods for mixing the separately generated mist and biocide gas include combining the mists in a Y-tube and then mixing the combination in a baffled mixing chamber, combining the mists in an area above their points of generation and then further mixing, and providing a series of mist generation units connected by a conduit for a carrier medium to pass to and connect the units and cause the mists to combine. Alternatively, the biocide may be released from a controlled source to dissolve in a generated solvent mist. Such controlled release of biocide includes providing a source of slow diffusion of chlorine dioxide gas to dissolve in water mist by convection and mixing, providing a continuous flow of chlorine dioxide solution via a coil reservoir for controlled contact with the mist, providing chlorine dioxide gas released from a solid-state mixture.

20 Claims, 6 Drawing Sheets

U.S. PATENT DOCUMENTS

| | | | |
|---|---|---|---|
| 5,290,524 A | * 3/1994 | Rosenblatt et al. | 422/305 |
| 5,407,656 A | * 4/1995 | Roozdar | 423/477 |
| 5,989,497 A | 11/1999 | Labonte, Jr. | |
| 2003/0143111 A1 | * 7/2003 | Cowley et al. | 422/37 |

OTHER PUBLICATIONS

Charles N. Haas, Decontamination Using Chlorine Dioxide, Hearings on "The Decontamination of Anthrax and Other Biological Agents", Nov. 8, 2001.

* cited by examiner

Figure 6

METHOD FOR BIOERADICATION USING FINE MIST OF BIOCIDE SOLUTIONS

PRIORITY CLAIM

The present invention claim benefit of the priority filing date of U.S. Provisional Patent Application No. 60/377,156 filed on May 2, 2002.

INTRODUCTION AND BACKGROUND OF THE INVENTION

1. Field of the Invention

The present invention relates to a device and method for using a stable chlorine dioxide solution in bioeradication processes such as sterilization, disinfection, and sanitation in various food, agricultural, hospital and medical industries. More specifically, the invention pertains to stabilizing a biocide agent in an atomized mist phase solvent to create a homogeneous gas-like mist for fumigation and sterilization of surfaces and volumes of all scales.

2. Description of Prior Art

A tremendous urge for the present invention comes from the November 2001 instances of anthrax decontamination of federal buildings and continued future threats of bioterrorism. Some specific instances involve anthrax delivered in sealed envelopes. Surprisingly, anthrax was found airborne, on surfaces and in contained volume spaces, such as sealed packages. Anthrax spores are on the order of 1-5 microns, which in turn can diffuse under favorable conditions of paper porosity, physical structure and time of exposure, pressure, temperature and flow conditions.

Based on the immediate necessity to decontaminate large volumes of the Hart Senate Building, the government used gaseous chlorine dioxide as a biocide. However, prior to this use of chlorine dioxide for such large volumes, the stability, toxicity and effectiveness of the chlorine dioxide gas for such application remained undetermined. Besides other problems, the chemical instability of chlorine dioxide gas in concentrations exceeding 1000 ppm in gas phase resulted in poor decontamination efficiency. In order to increase the effectiveness of chlorine dioxide gas in decontamination, steam was flushed into the treatment area to increase the humidity and help stabilize the chlorine dioxide gas.

Chlorine dioxide has attracted considerable attention for its use in sterilization, disinfection, and sanitation due its superior properties. In particular, chlorine dioxide is relatively less toxic in a solution with water compared to free chlorine and bleach solutions. Chlorine dioxide does not react to form other chemicals when dissolved in water, an attractive advantage compared to other chlorine containing bleaching agents. However, chlorine dioxide is not very stable as a gas, making its use in gaseous state as a biocide and its storage and transportation very problematic.

Hence, because of the chemical instability of chlorine dioxide gas at relatively high concentrations, its use as a disinfectant/sanitizer is less common compared to its use in solution form. Gaseous chlorine dioxide as a disinfectant for surfaces and implements is disclosed in U.S. Pat. Nos. 4,908,188, 4,681,739 and 4,504,442 and has been studied for application in the food processing and poultry industries. All of these prior attempts to stabilize and apply chlorine dioxide gas have found that better disinfection is obtained at very high humidity levels (80%), indicating the need to stabilize the chlorine dioxide gas using moisture or humidity similar to the outcome in the Hart Senate building case in which steam was injected into the building.

U.S. Pat. No. 5,989,497 to Roland R. Labonte, Jr. proposes using a mist of chlorine dioxide solution generated by high-pressure atomization to deodorize malodorous substances. However, Labonte does not discuss recently discovered issues concerning the separation of chlorine dioxide from the solution during atomization and the resulting instability of the separated chlorine dioxide biocide agent. Electrostatic, high-pressure, or ultrasonic atomization leads to gas separation of the chlorine dioxide from the liquid solution. Ambient pressure ultrasonic atomization is the most attractive way of generating a mist solution of biocide without using pressure or electric charge or heat, but the mechanics of the ultrasonic wave propagation still causes the chlorine dioxide to distill as gas. The distilled gas escapes as the unstable chlorine dioxide gas substance, prior to the atomization of the water inside the mist generator. When Chlorine dioxide solution is atomized using widely used methods such as electrostatic and pressure atomization technologies, the gas separates from the solution, leaving behind water or the solvent. As such, these methods cannot be effectively utilized to produce aqueous chlorine dioxide mist. Moreover, pressure atomization of chlorine dioxide solution is not safe and can be explosive at high enough concentration.

Thus, Labonte does not provide a complete solution to the stabilization problem and a continuing need exists for obtaining a stable mist of chlorine dioxide dissolved in a solvent such as water that is highly effective in sterilization and the like. Because chlorine dioxide decomposition is primarily responsible for the substance's power in oxidizing organic matter, microorganisms, bacteria, and bacterial spores, a need exists to provide chlorine dioxide in a stable form in which the chlorine dioxide will not rapidly decompose prior to it interacting with the desired treatment site. A gas phase or pseudo-gas phase means for providing and using stable chlorine dioxide is needed to provide a mobile chlorine dioxide solution efficient in the treatment of rooms and buildings or smaller-scale applications. Such a means for applying chlorine dioxide as a biocide agent should avoid using potentially damaging levels of humidity or temperature or dangerous high-pressure delivery systems.

SUMMARY OF INVENTION

This invention addresses the instability of dry chlorine dioxide gas as a chemical by providing a means for bioeradication using a fine mist solution of an otherwise unstable gaseous biocide agent such as chlorine dioxide. Chlorine dioxide is referred to throughout this application as the biocide of choice. However, other suitable biocide agents soluble or stabilized by the mist solvent and practical for bioeradication may be used. Generally though, the method provided will produce a stable aqueous solution of chlorine dioxide mist for sterilizing, disinfecting, or sanitizing.

The homogeneous aqueous solution of the present mist includes a solvent such as water, and a biocide agent such as chlorine dioxide, which would otherwise be unstable. The unstable biocide agent or chlorine dioxide is quickly dissolved or mixed while in mist phase with the solvent or water mist causing the biocide agent to co-exist or co-mist with the solvent or water. The water mist microencapsulates the chlorine dioxide so that it does not decompose in the fumigation volume or space. The resulting homogenous mist solution provides a mist for delivering the biocide agent in a chemically stable form in an aqueous or nonaqueous phase.

The homogeneous mist solution is created by separately generating a mist of chlorine dioxide in aqueous or non-aqueous form and generating a mist of water solvent. Within an appropriate time before the chlorine dioxide decomposes, the two separately generated mists are combined via a suitable method to form the homogenous mist with the chlorine dioxide mixed or dissolved into the water mist such that the chlorine dioxide within each droplet is encapsulated by water. Methods for mixing the two pre-generated mists include: (a) combining the mists in a Y-tube and then mixing the combination in a baffled mixing chamber; (b) combining the mists in an area above their points of generation and then further mixing; and (c) providing a series of mist generation units connected by a conduit for a carrier medium to pass to and connect the units and cause the mists to combine.

Alternatively, providing a controlled source of chlorine dioxide to a generated water mist may create the homogeneous mist solution. Several alternative embodiments include: (d) providing a source of slow diffusion of chlorine dioxide gas dissolved in water mist; (e) providing a continuous flow of chlorine dioxide solution via a coil reservoir whereby the chlorine dioxide has controlled contact with the mist generating reservoir; and (f) providing controlled release of chlorine dioxide from a solid-state mixture to the water mist droplets.

Meanwhile, each method will provide mist droplets of the mist solution that are very fine and promote the behavior of the aqueous mist as a pseudo-gas phase biocide agent. The pseudo-gas agent penetrates corners and crevices during surface and volume fumigation using the method discussed. The pseudo-gas phase mist solution described consists of extremely small droplets of the chlorine dioxide solution. The very small diameter droplets may be less than one micron in diameter, and the small droplets greatly increase the total reactive surface area of the mist, which increases the reactivity and effectiveness of the mist as a biocide agent. Further, the very small diameter droplets have increased reactivity due to the molecular cluster arrangements situated about the surface of the droplets.

The mist fog so generated is extremely reactive and smaller in diameter compared to spores of anthrax or other biological contaminants. The mist fog provides for the ready chemical destruction of cells by providing chlorine dioxide in a favorable concentration via the mist to a contaminated surface or volume. The mist may be delivered by free or forced convection flow to the desired location where the mist solution promotes adequate residence time for the biocide agent to allow effective treatment.

DETAILED DESCRIPTION OF INVENTION

Referring now to the figures, a method and device for bioeradication using fine mist of gaseous biocide solutions is shown in various embodiments, which overcome the problem of gas separation of gaseous biocide from a solution with a solvent such as water. Chlorine dioxide is the primary biocide agent considered and has been found very effective for sterilizing, disinfecting, and sanitizing, but exhibits the known problem of instability caused by gas separation prior to reaching the treatment site. Chlorine dioxide may be used in lieu of biocide or biocide agent throughout the detailed description. Likewise, water or water mist will be used interchangeably with the term solvent.

A method of creating a fine mist of stable chlorine dioxide or biocide solution is disclosed for sterilizing, disinfecting, or sanitizing. The chemical biocide used in the desired sterilizing solution is not restricted to chlorine dioxide but may include other biocide gases and their mixtures or a highly volatile biocide liquid that vaporizes at near ambient or higher temperature. One important example of an alternative biocide solution that may be used in the present invention includes a mixture of chlorine dioxide and hydrogen peroxide solution. Because of synergistic effects, this mixture may provide a powerful sterilizing agent without usual adverse side effects such as bleaching or producing harmful chemical byproducts. Further, the solvent of the fine mist solution in which the biocide is dissolved may be any suitable organic or inorganic mist phase material and may include additive material including solids.

In general the biocide gas is released from a source such as a reservoir of liquid solution 10. For example, chlorine dioxide may be released from chlorine dioxide source 12 such as a liquid chlorine dioxide solution. Alternatively, chlorine dioxide could be supplied via release from a solid-state chlorine dioxide source. If provided in a liquid solution, the concentration of chlorine dioxide in liquid phase will typically be about 500 to 2000 ppm, while the gas or mist solution phase portion of chlorine dioxide would depend upon the total volume of fumigation and density of gas. Thus, the biocide agent may be provided in an aqueous mist phase created by processes similar to those discussed below for the solvent material or in a nonaqueous gas phase.

Meanwhile, separate from the release of biocide mist or gas, the liquid mist phase solvent or water mist is generated from a liquid reservoir 10 of a suitable organic or inorganic solvent. The desired solvent will depend upon the application and the solubility of chlorine dioxide or biocide therein. From the solvent reservoir 10, atomizing the liquid material creates the solvent mist 48. In the embodiments discussed, it has been found preferable to use an ambient pressure ultrasonic device 20 to atomize the liquid solvent.

After the biocide agent and solvent are separately generated they are released to a mixing chamber 16 or space provided for combining the biocide agent with the mist phase solvent. As the agents are combined, the chlorine dioxide droplets or gas are dissolved or combined via a suitable method with droplets of solvent or water such that the two agents co-exist or co-mist. The entire process of dissolving or encapsulating the chlorine dioxide droplets in water occurs very quickly within an appropriate time before the biocide decomposes and loses its effectiveness as a sterilizing agent. The combination of the biocide and solvent occurs while both materials are in the mist phase.

Figure 1:
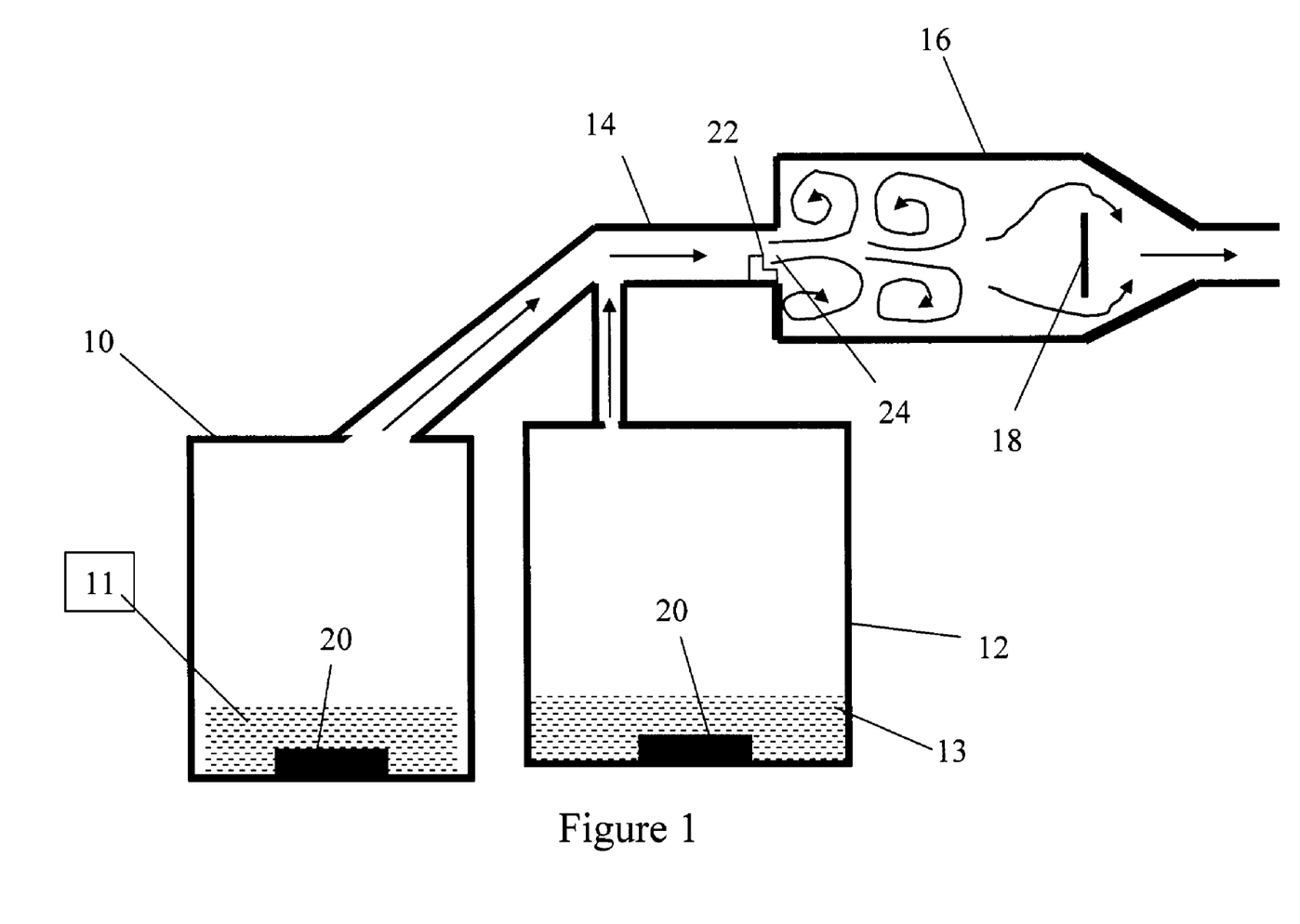
FIG. 1 is a schematic illustration of a device in accordance with one embodiment of the invention, wherein co-streams of water mist and chlorine dioxide gas are produced from their respective reservoirs.
Figure 2:
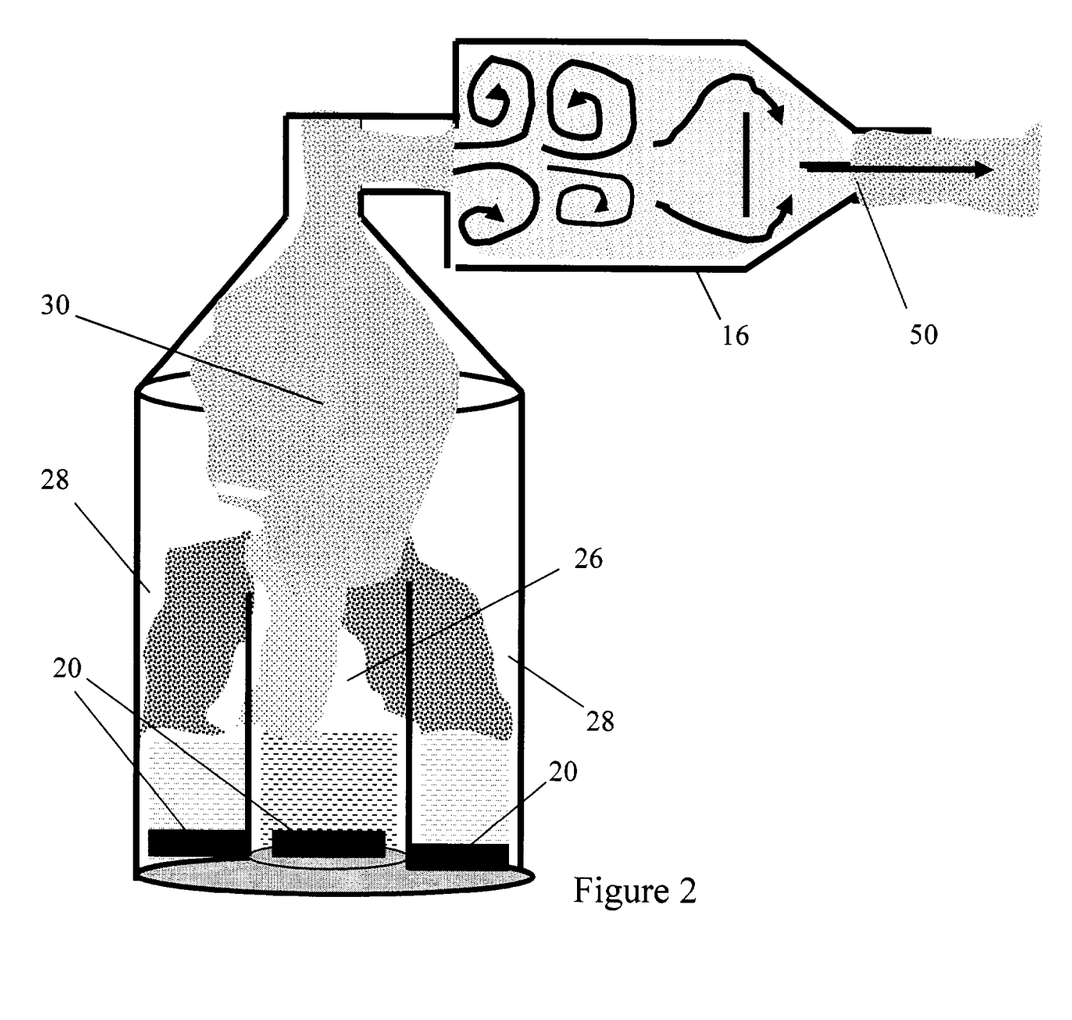
FIG. 2 is a schematic illustration of a device in accordance with one embodiment of the invention, wherein water mist is produced in an annular section of a column and chlorine dioxide gas is produced in a central section of the column.

The mixing and dissolving of the chlorine dioxide droplets or gas with the water mist may be increased by the use of premixing mechanism, such as the baffled premixing chamber 16 shown in FIGS. 1 and 2. As the mixing occurs, water molecules within the combined droplets surround the chlorine dioxide, such that the water microencapsulates the chlorine dioxide. The combination and dissolving of the biocide in the water mist prevents the biocide from decomposing prior to contacting the treatment site, and creates a homogeneous solution for use in treating contaminated areas. The homogeneous solution of stabilized chlorine dioxide dissolved in fine mist droplets of water may be used as a nearly gas phase fumigating agent because the mist solution promotes adequate residence time for the biocide agent to allow effective treatment for sterilizing, disinfecting, or sanitizing. Otherwise, chlorine dioxide in the desirable gas phase would not be an efficient agent for sterilization due to decomposition.

The preferred mist creation and extraction strategy is to use a high frequency ultrasonic device such as a piezoelectric transducer 20 of up to 9 inches diameter to atomize the liquid held in the related reservoirs. This strategy may be used with respect to both the solvent and the biocide agents. To create a very fine mist, the frequency of oscillation of the transducer may be up to 20 MHz or more.

The quality of the mist is maintained by using sufficient frequency and conditions to produce a plume of mist having a high number of very small droplets concentrated about the exterior portions of the flume. Primarily nanoscale droplets of less than one micron in diameter may be provide for by extracting the droplets from the flume using a swirling carrier gas that is applied tangential to the extraction column to entrain only the smaller droplets. The larger droplets may be left in the center of the flume to fall back into the reservoir of solution as a fountain of water. Extracting only the finest droplets for combination to form the biocide mist solution further promotes the desirable pseudo-gas characteristics of the mist solution. The final mist solution may be delivered to the desired treatment location by free or forced convection flow.

The throughput of mist solution is variable and scalable using variations of frequency and oscillator surface area. Delivery devices may be designed for application by hand to small areas, for medium scale applications suitable for devices designed to be carried by backpack, or for large-scale applications delivered to entire rooms or buildings. In small-scale applications, a hand-held applicator may have mist throughput of a few milliliter per minute. Whereas, in larger-scale volume applications, applicators may have a larger throughput capacity of a several liters per minute, which would be advantageous for decontamination of rooms and buildings contaminated with bacterial spores such as that encountered in year 2001 in Hart Senate Building due to anthrax contamination.

The desired fine mist biocide solution will have certain characteristics that make the mist preferable. For instance, as suggested, the desired mist will contain droplets of very small size. In particular, the preferable mist in many applications should contain a large portion of droplets that are about one micron or sub-micron in scale. Moreover, droplet diameter size in the range 50 to 1000 nanometer is desirable to promote the behavior of the aqueous mist as a pseudo-gas phase biocide agent. The pseudo-gas aqueous mist agent provides improved quality of treatment by infiltrating all areas in a volume, much like a gas, and penetrating corners and crevices during both surface and volume fumigation.

Additionally, the very small diameter droplets of less than one micron in diameter greatly increase the total reactive surface area of the mist, which increases the reactivity and effectiveness of the mist as a biocide agent for bacterial disinfection. The very small diameter droplets also have increased reactivity due to the molecular cluster arrangements situated about the surface of the droplets as opposed to being situated toward the interior of the droplets, making it easier for the chemical reactions involving the biocide agent to occur with outside contaminants. The large mist surface area of several square meters per a liter of aqueous solution used provides the advantage of about 1500 times volume expansion from the liquid compared to mist-phase. Due to the expansion, a smaller quantity of biocide agent is used providing for conservation of the expensive biocide chemicals.

Figure 5:
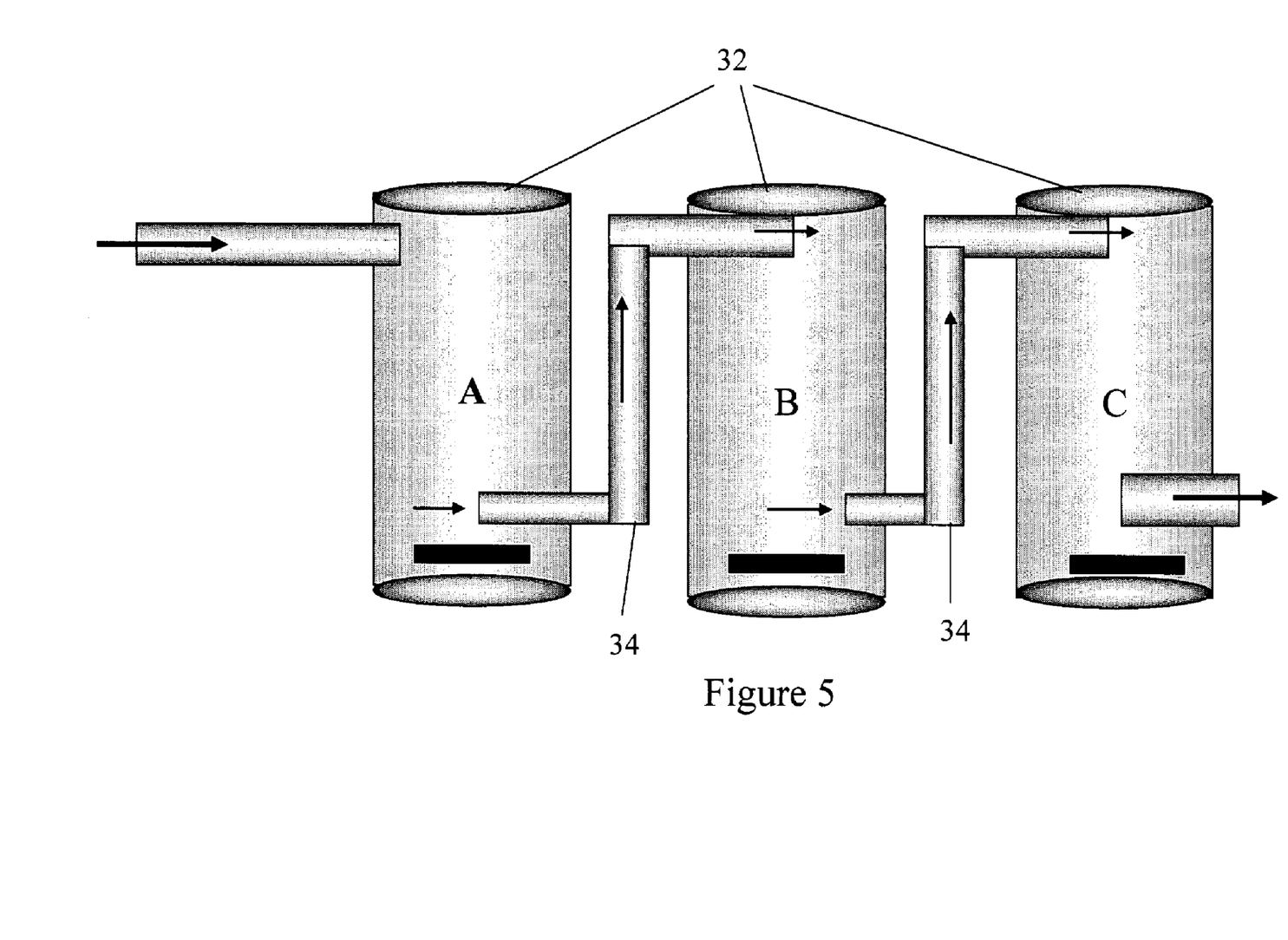
FIG. 5 is a schematic illustration of a device in accordance with the invention depicting a modular mist generation system arranged in series for dissolving chlorine dioxide gas in a solvent mist via a succession solvent mist generators.

Various embodiments of the invention are provided that use the process described to achieve a stable chlorine dioxide mist stream. First, the embodiments illustrated in FIGS. 1, 2, and 5 provide apparatuses for mixing the two pre-generated mists of biocide agent and solvent. The co-streams of water mist and chlorine dioxide gas are produced simultaneously, but separately, from their respective reservoirs. The chlorine dioxide solution is subjected to ultrasonic waves in a mist generation unit whereby the cavitations process liberates the chlorine dioxide gas from the solution and into a chamber.

In FIG. 1, each co-stream of mist and gas is then combined in a Y-tube 14 creating a partially mixed stream. The resulting combination of chlorine dioxide gas and water mist is then mixed further in a baffled pre-mixing chamber 16. The pre-mixing chamber 16 has a backward-facing step 22 for creating a vortex flow for mixing at the entrance 24, and a downstream baffle 18 furthers the mixing process to ensure adequate absorption of the chlorine dioxide gas by the solvent water mist. This process produces a homogeneous mixture of ClO2 and water. The solubility of chlorine dioxide in water provides a favorable condition for chlorine dioxide to be dissolved in droplets of water mist, providing an efficient method to stabilize the gas phase chlorine dioxide.

In FIG. 2 a centrally symmetric two-stream approach is provided by the apparatus that combines the separately generated co-streams of water mist and chlorine dioxide gas in an area above their points of generation. In this method, the water mist and chlorine dioxide are generated in columns having a concentric cylindrical geometry. The central, innermost section 26 of the column provides a reservoir of solution from which chlorine dioxide is generated. Simultaneously, the outer annular section 28 of the column provides a reservoir of water for producing the water mist. The water mist and ClO2 streams mix above the concentric columns where the streams converge into one area or chamber 30 external from the generating columns 26 and 28. This method makes available a larger mixing volume just above the concentric section before the combination of mist and gas is exhausted from the extractor or generator via the outlet 50. Further, the larger mixing volume provides significant residence time for the chlorine dioxide to dissolve in the available water mist. After it is exhausted, the resulting mixture then passes through a pre-mixing chamber as described previously in FIG. 1 where, because of the mixing vortex and baffle assisted re-circulating flow, a significant quantity of ClO2 is dissolved in the water mist droplets.

As shown in FIG. 5 the chlorine dioxide solution mist generator may be configured to provide a series of mist generation units 32 connected by a conduit 34 for a carrier medium to pass through and connect the units. As the carrier medium passes through the conduit connecting the unit, the water mist and biocide gas will combine. For example, a first unit A in the series containing a reservoir of chlorine dioxide solution may generate moist chlorine dioxide and water mist from the solution and be conveyed along with the carrier gas, air. A second mist generation unit B containing a reservoir of pure water may produce pure water mist. The pure water mist is then extracted by the inlet carrier medium of moist chlorine dioxide. The chlorine dioxide gas dissolves in the mist droplets and the mixture moves into subsequent water mist generators C as desired. A desired concentration of ClO2 dissolved in the water mist phase may be achieved for particular application using this modular mist generator approach, as successive mist generator can put more and more water for dissolving chlorine dioxide. Alternatively, the first unit may produce mostly gaseous ClO2 that would enter into the second unit producing pure water mist. Then, the ClO2 gas would dissolve into the water mist droplets providing stable chlorine dioxide in a homogeneous mist solution.

Figure 3:
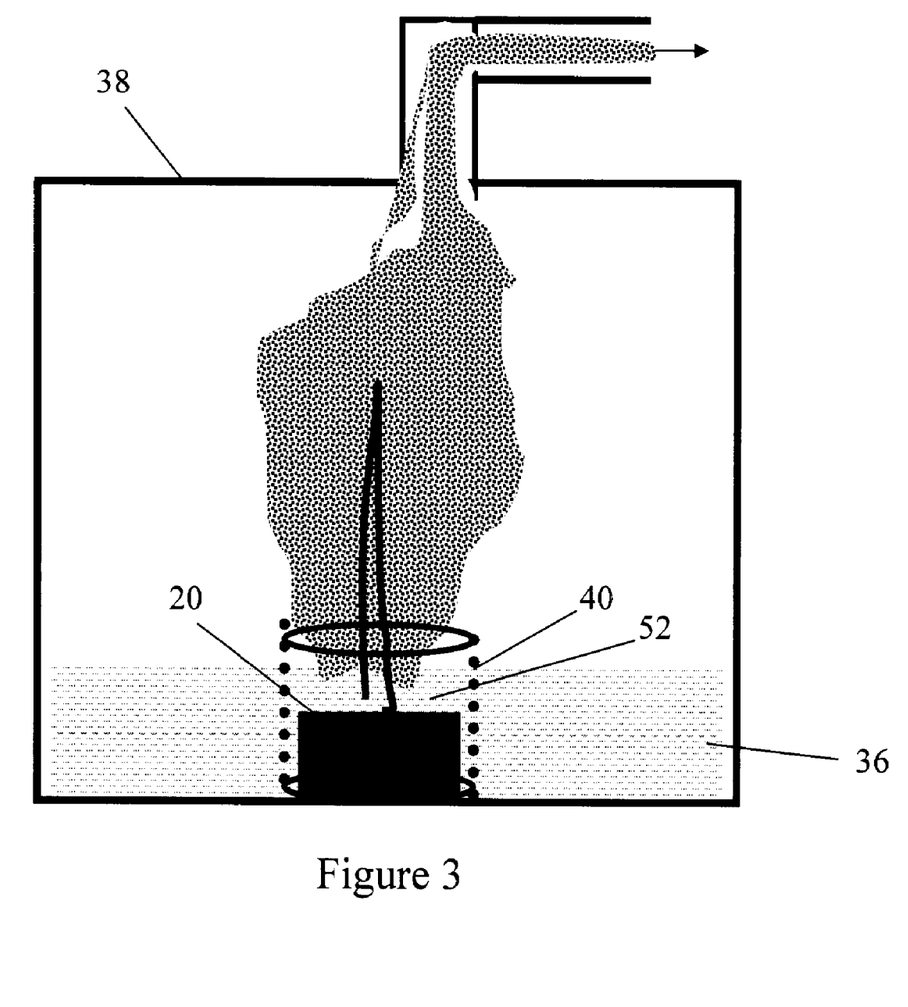
FIG. 3 is a schematic illustration of a device in accordance with an embodiment of the invention having a liquid volume of biocide solution situated in a reservoir for supplying the biocide via concentration diffusion of biocide gas from the liquid solution.
Figure 4:
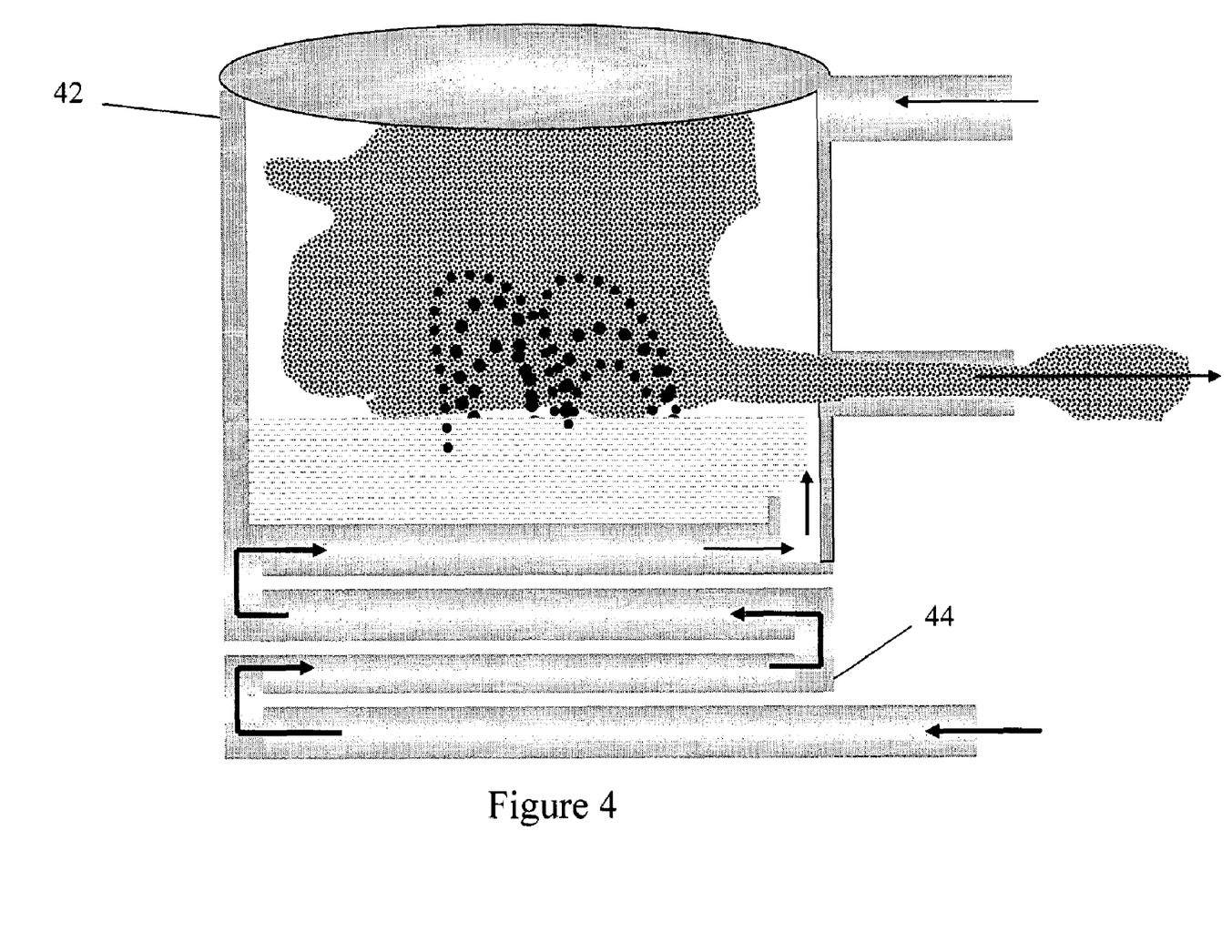
FIG. 4 is a schematic illustration of a device in accordance with one embodiment of the invention wherein a coiled-tube provides a reservoir of biocide solution.
Figure 6:
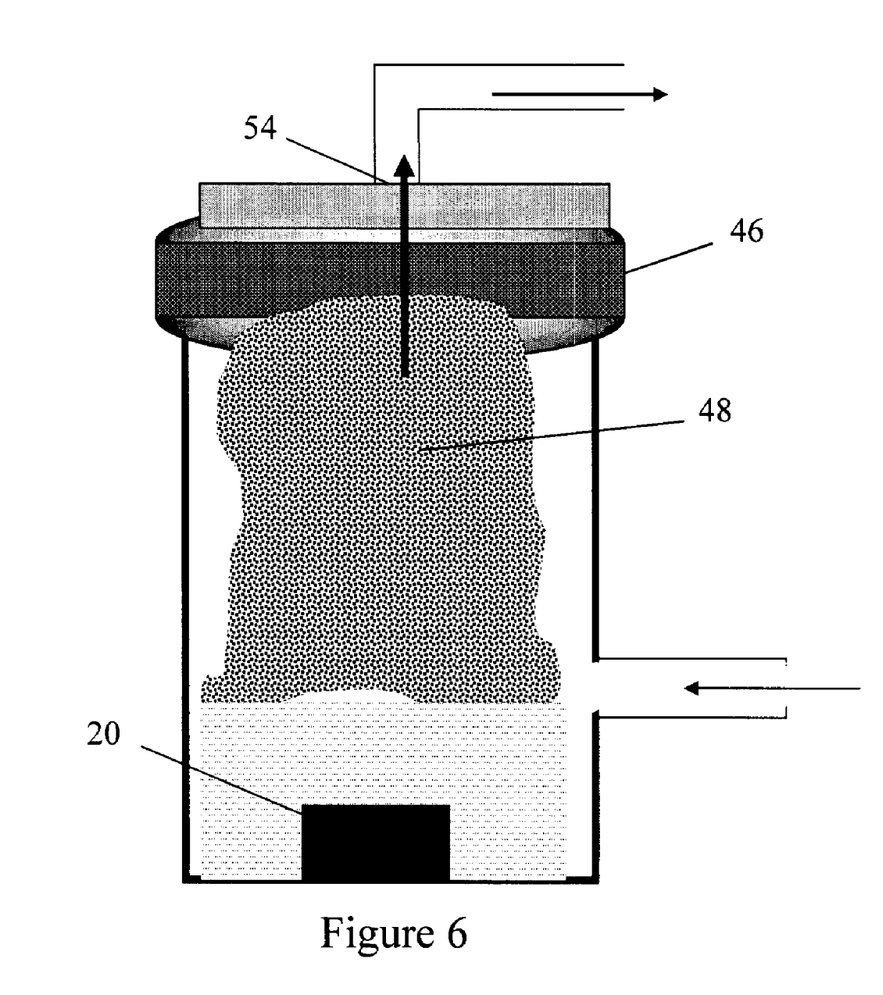
FIG. 6 is a schematic illustration of a device of the invention showing the controlled release of chlorine dioxide from a solid-state source.

Alternatively, the embodiments in FIGS. 3, 4, and 6 each provide a controlled source of chlorine dioxide gas to a generated water mist to create the homogeneous mist solution. FIG. 3 depicts a continuous flow of chlorine dioxide from a solution 36 in a mist generator 38. This continuous flow generator provides a continuous source for the slow diffusion of chlorine dioxide gas into the solvent mist where the ClO2 dissolves into the water mist by convection and further mixing. In this method, the transport of chlorine dioxide to the local cavitations area is mainly by a concentration gradient driven diffusion process, which is usually very slow compared to cavitations and mass loss rate. Convection is minimized by the stagnant chlorine dioxide solution and by including a flow-guard, flow-shield, or a porous screen wall 40 around the ultrasonic transducer 20. When cavitations resume, water mist is produced, and at the same time, the chlorine dioxide depletion due to distillation is replenished by the diffusion of ClO2 from the vicinity by the slow diffusion process. On average, ClO2 will always be available to combine with the water mist. Although not significant, any convection assisted flow guards will minimize ClO2 transport to the cavitations area. In this method, chlorine dioxide gasification from solution is restricted by its supply to the area by slow diffusion process.

FIG. 4 illustrates a continuous flow mist generator 42 that provides chlorine dioxide solution via a coiled tube reservoir 44. The coiled tube reservoir 44 supplies the solution on demand at a controlled release rate depending on the mass loss rate. The controlled release provided by the coiled tube reservoir serves well to enable continuous fumigation. Providing a continuous flow of chlorine dioxide solution via a coil reservoir 44 enables controlled contact of the chlorine dioxide with the mist-generating reservoir 52. Changing the size and effective length of the tube 44 is useful in varying the reservoir size. The desired reservoir properties depend on the volume of chlorine dioxide mist solution to be used during fumigating. A unique feature of this technology is to be able to restrict chlorine dioxide de-gassing by cavitations by releasing it only by slow diffusion process. The chlorine dioxide solution in contact with the cavitating volume is limited to a few inches but the entire volume is contained within the tube at a few feet away from the local cavitations area. The only way ClO2 species can reach the cavitating location is by diffusion because bulk convection velocity is nearly absent and the solution stagnant. A moving boundary may operate to keep the level of the liquid in the reservoir constant by replenishing the liquid therein.

In yet another embodiment, a controlled release of chlorine dioxide from a solid-state mixture 46 may be provided to mix with water mist droplets interacting therewith. FIG. 6 shows one way to dissolve chlorine dioxide released from solid-state reactions into a water mist solvent in which oncoming water mist droplets 48 at the outlet location 54 quickly absorb ClO2 gas released from a solid-state pouch 46. Proprietary methods exist to prepare ClO3 gas on demand by mixing solid-state chemical reactants that are then stored in pouches. Upon shaking the pouch or using other means of activation, ClO2 gas is released. Thus, the solid-state chlorine dioxide source is stored at the solvent mist outlet 54 where the released ClO2 will come into contact with the mist 48. The mist outlet may be located on the lower portion of the mist-generating device, just above the liquid reservoir level. The methodology discussed is applicable to other sources of chlorine dioxide where a solvent mist flowing across the ClO2 flow region can quickly absorb liberated ClO2.

The present invention provides several advantages for sterilizing, decontaminating, and disinfecting volumes using chlorine dioxide or other unstable gaseous biocide. Stabilizing chlorine dioxide biocide by the methods provided provides a sterilizing method capable of killing bacteria, anthrax, black mold or other biological contaminants, within a very short time interval, often less than one hour, without requiring excessive control of air-leaks. In other words, these type biocides can be used safely in buildings with reasonably secured ventilation, while being sufficient to achieve effective sterilization. The biocide method provided may be used for sanitation of poultry, beef or other foods that may have biological contaminants. Further, the mechanical infrastructure to implement the methods and apparatus required by the invention is simple, inexpensive and can be quickly assembled for fumigation. No pumps, pipelines, motors, heavy machinery items, or trucks are needed. Finally, the methods disclose a system controllable to provide for favorable mist density, free or forced convection flow conditions, adequate residence time, mist concentration, humidity, temperature and pressure.

We claim:

1. A method for sanitizing, decontaminating or disinfecting including the steps of:
    a. providing a solvent;
    b. providing a biocide source of biocide agent;
    c. generating a mist of the solvent;
    d. releasing a biocide gas or vapor from the biocide source;
    e. introducing the mist to the biocide gas or vapor;
    f. mixing the mist and biocide gas or vapor to dissolve the biocide gas or vapor therein and create a biocide mist solution; and
    g. delivering the biocide mist solution to a treatment site for sanitizing, decontaminating, or disinfecting the site.

2. A method for sanitizing, decontaminating or disinfecting as in claim 1 in which the step of generating a mist of the solvent includes generating the mist at ambient pressure using an ultrasonic wave generating device to atomize the solvent.

3. A method for sanitizing, decontaminating or disinfecting as in claim 1 in which the solvent is water.

4. A method for sanitizing, decontaminating or disinfecting as in claim 1 in which the biocide agent includes chlorine dioxide.

5. A method for sanitizing, decontaminating or disinfecting as in claim 1 in which the steps of generating the mist of solvent and releasing the biocide gas or vapor from the biocide source occur simultaneously, but separately.

6. A method for sanitizing, decontaminating or disinfecting as in claim 1 in which the step of mixing the mist and the biocide gas or vapor to dissolve the biocide gas or vapor therein and create the biocide mist includes combining the mist and the biocide gas or vapor in a Y-tube.

7. A method for sanitizing, decontaminating or disinfecting as in claim 1 in which the step of mixing the mist and the biocide gas or vapor to dissolve the biocide gas or vapor therein and create the biocide mist solution includes the step of premixing the mist and the biocide gas or vapor in a baffled premixing chamber.

8. A method for sanitizing, decontaminating or disinfecting as in claim 1 in which the step of generating a mist of solvent include providing a series of mist generating units connected by a conduit for a carrier medium, and the step of mixing the mist and the biocide gas or vapor to dissolve the biocide gas or vapor therein and create the biocide mist solution includes passing the carrier medium through the conduit and causing the mist to mix with the biocide gas or vapor.

9. A method for sanitizing, decontaminating or disinfecting as in claim 1 in which the biocide source is a liquid phase reservoir of chlorine dioxide solution.

10. A method for sanitizing, decontaminating or disinfecting as in claim 1 in which the biocide source is a continuous flow of chlorine dioxide solution via a coil reservoir.

11. A method for sanitizing, decontaminating or disinfecting as in claim 1 in which the biocide source is a solid-state material for releasing chlorine dioxide.

12. A method for sanitizing, decontaminating or disinfecting as in claim 1 in which the biocide agent includes a chlorine dioxide and hydrogen peroxide.

13. A method for sanitizing, decontaminating or disinfecting as in claim 1 in which the mist is composed substantially of droplets of less than one micron in diameter.

14. A method for sanitizing, decontaminating or disinfecting as in claim 1 in which the mist is composed substantially of droplets have a diameter in a range of 50 to 1000 nanometers.

15. A method for sanitizing, decontaminating or disinfecting as in claim 1 in which the treatment site is a building.

16. A method for sanitizing, decontaminating or disinfecting as in claim 15 in which the building is contaminated with anthrax.

17. A method for sanitizing, decontaminating or disinfecting including the steps of:
   a. providing a solvent;
   b. providing a biocide source of biocide agent;
   c. generating a mist of the solvent and extracting smaller droplets from a column of the mist using a swirling flow of carrier gas that is applied tangential to the column to entrain only the smaller droplets;
   d. releasing a biocide gas or vapor from the biocide source;
   e. introducing the mist to the biocide gas or vapor;
   f. mixing the mist and biocide gas or vapor to dissolve the biocide gas or vapor therein and create a biocide mist solution; and
   g. delivering the biocide mist solution to a treatment site for sanitizing, decontaminating, or disinfecting the site.

18. A method for sanitizing, decontaminating or disinfecting including the steps of:
   a. providing a reservoir of water;
   b. providing a reservoir of chlorine dioxide solution;
   c. providing an outer cylindrical column;
   d. providing an inner cylindrical column concentric to the outer cylindrical column;
   e. generating a water mist in the outer cylindrical column from the reservoir of water;
   f. generating a release of chlorine dioxide gas in the inner cylindrical column from the reservoir of chlorine dioxide solutione;
   g. mixing the water mist and chlorine dioxide gas externally from the concentric columns to create a biocide mist solution; and
   h. delivering the biocide mist solution to a treatment site for sanitizing, decontaminating, or disinfecting the site.

19. A method for sanitizing, decontaminating or disinfecting as in claim 1 in which the treatment site is poultry, beef, or food.

20. A method for sanitizing, decontaminating or disinfecting as in claim 1 in which the treatment site is contaminated with black mold.

* * * * *